United States Patent [19]

Nádor et al.

[11] Patent Number: 4,769,373
[45] Date of Patent: Sep. 6, 1988

[54] ANTI-ARRHYTHMIC AZABICYCLIC COMPOUNDS

[75] Inventors: Károly Nádor; Gábor Kraiss; Margit Paróczay; Egon Kárpáti; László Szporny, all of Budapest, Hungary

[73] Assignee: Richter Gedeon Vegyeszeti Gyar Rt., Budapest, Hungary

[21] Appl. No.: 674,773

[22] Filed: Nov. 26, 1984

[30] Foreign Application Priority Data

Nov. 30, 1983 [HU] Hungary .............................. 4096/83

[51] Int. Cl.⁴ .................... C07D 221/22; A61K 31/44
[52] U.S. Cl. ..................................... 514/299; 546/183
[58] Field of Search ......................... 546/183; 514/299

[56] References Cited

FOREIGN PATENT DOCUMENTS 1195746  6/1970  United Kingdom .

Primary Examiner—John M. Ford
Assistant Examiner—Bernard I. Dentz
Attorney, Agent, or Firm—Herbert Dubno; Jonathan Myers

[57] ABSTRACT

The invention relates to new anti-arrythmic azabicyclo[3.3.1]nonanes of the general formula (I)

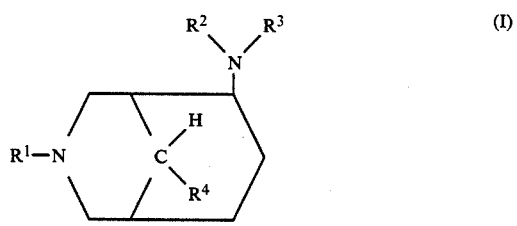

wherein
$R^1$, $R^2$ and $R^3$ are $C_{1-4}$ alkyl groups which are the same or different, or one of them is a benzyl group and the others are $C_{1-4}$ alkyl groups, and
$R^4$ is a hydroxy group, or an etherified hydroxy group of the formula —$OR^5$, or an esterified hydroxy group of the formula —$OOCR^6$, in which the esterifying group
$R^5$ is a phenyl or benzyl group which optionally each can have a trihalomethyl substituent or one or more halogen or $C_{1-4}$ substituents, or is a diphenyl or benzhydryl group, and the esterifying group
$R^6$ is a $C_{1-8}$ alkyl or a $C_{3-6}$ cycloalkyl group, or a phenyl or benzyl group which optionally each can have a halo-substituent or one or more $C_{1-4}$ alkyl, $C_{1-4}$ alkoxy, nitro or phenyl substituents, or is an optionally halogenated or hydrogenated naphthyl group, or a cinnamyl group optionally substituted by a halogen atom or $C_{1-4}$ alkoxy groups, or is a benzhydryl or 1,1-diphenyl-hydroxymethyl group, or is a heterocyclic substituent selected from the group consisting of thenyl, 9-xanthenyl or 3-indolyl-($C_{1-3}$ alkyl) groups, as well as the stereoisomers and pharmaceutically acceptable acid addition salts thereof.

The invention also provides a process for the preparation of the new compounds of the general formula (I), in which new intermediates of the general formula (IV),

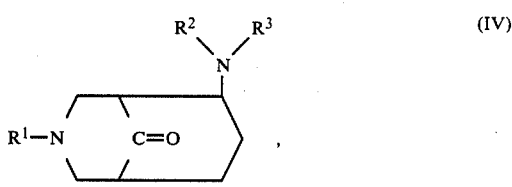

wherein $R^1$, $R^2$ and $R^3$ are as defined above, are utilized.

9 Claims, No Drawings

ANTI-ARRHYTHMIC AZABICYCLIC COMPOUNDS

FIELD OF THE INVENTION

The invention relates to new azabicyclo[3.3.1]nonanes of the formula (I)

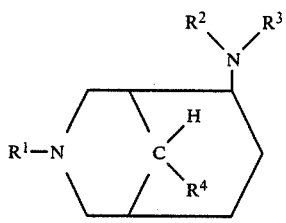
(I)

wherein
- $R^1$, $R^2$ and $R^3$ are $C_{1-4}$ alkyl groups which are the same or different, or one of them is a benzyl group and the others are $C_{1-4}$ alkyl groups, and
- $R^4$ is a hydroxy group, or an etherified hydroxy group of the formula $-OR^5$, or an esterified hydroxy group of the formula $-OOCR^6$ in which the etherifying group
- $R^5$ is a phenyl or benzyl group which each can have a trihalomethyl substituent or one or more halogen or $C_{1-4}$ alkyl substituents, or is a diphenyl or benzhydryl group, and the esterifying group
- $R^6$ is a $C_{1-8}$ alkyl or a $C_{3-6}$ cycloalkyl group, or a phenyl or benzyl group which each can have a halosubstituent or one or more $C_{1-4}$ alkyl, $C_{1-4}$ alkoxy, nitro or phenyl substituents, or can be an halogenated or hydrogenated naphthyl group, or a cinnamyl group which can be substituted by a halogen atom or $C_{1-4}$ alkoxy groups, or is a benzhydryl or 1,1-diphenyl-hydroxymethyl group, or is a heterocyclic substituent selected from the group consisting of thenyl, 9-xanthenyl or 3-indolyl-($C_{1-3}$ alkyl) groups, as well as the stereoisomers and pharmaceutically acceptable acid addition salts thereof. The invention also relates to a process for the preparation of the new compounds.

The new compounds of the formula (I) can be distinguished from those known in the art both by the dialkylamino or N-alkyl-N-benzylamino group in position 6 of the skeleton and by the excellent anti-arrhythmic activity thereof.

BACKGROUND OF THE INVENTION

Azabicyclo[3.3.1]nonanes known in the art possess heterocyclic or N-(mono-butylamino) substituent in position 6 and show quite different effect, if any. Conformation studies of 6-(N-butylamino)-azabicyclononanes are reported by A. Z. Britten and J. O'Sullivan [Chem. and Ind. 15, 336 (1972)] without mentioning any utility of the said compounds. 6heterocyclic-azabicyclononanes with analgesic and anti-pyretic effects are described in non-examined Japanese patent application No. 42-25896 and with hypoglycemic and CNS stimulant activities in French patent specification No. 1,557,671.

DESCRIPTION OF THE INVENTION

It has been found that when a tetrahydropyridine derivative of the formula (V)

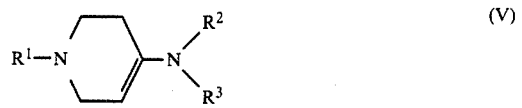
(V)

is reacted with acrolein in a manner known per se, a new 9-one compound of the formula (IV) is obtained

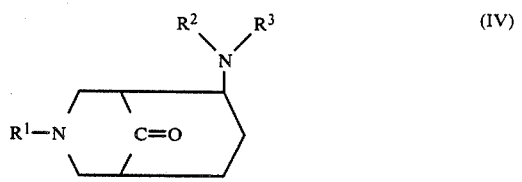
(IV)

—in the above formulae $R^1$, $R^2$ and $R^3$ are as defined above—. The resulting compound of the formula (IV) is then subjected to reduction to yield a new 9-ol compound of the formula (I), in which $R^4$ stands for hydroxy group and $R^1$, $R^2$ and $R^3$ are as defined above.

The 9-ol compound so obtained can then be etherified by using an etherifying agent of the formula (III),

(III)

or esterified with a carboxylic acid of the formula (II) or a reactive derivative thereof capable of acylation

(II)

to yield further new compounds of the formula (I) wherein $R^4$ is an etherified or esterified hydroxy group as defined above. In the formula (II) $R^6$ and in the formula (III) $R^5$ are as defined above and X means a halogen atom.

The starting materials of the formula (V) are new, with the exception when $R^1$, $R^2$ and $R^3$ are hydrogen atoms, and can be prepared by reacting an amine of the formula (VII)

(VII)

wherein $R^2$ and $R^3$ are as defined above, with a piperidone derivative of the formula (VI),

(VI)

wherein $R^1$ is a defined above. Detailed description of the preparation of the starting materials is given in the Examples.

The new compounds of the formula (I) are pharmaceutically active and primarily are useful in the treatment of cardiac rhythm disorders. The anti-arrhytmic effect was tested in Wistar rats. The animals first received aconitine intravenously to provoke disorders of the cardiac rhythm [M. Fekete and J. Borsy: Med. Exp. Basel, 10, 93 (1964)] and then i.v. the test (or reference) compound. The reference compound was Lidocaine. The dose required to restore the rhythm in 50% ($ED_{50}$ mg/kg) was determined.

Acute toxicities were tested in mice i.v. and the dose causing 50% mortality was determined both for the test compounds and for the reference (Lidocaine).

The results are listed in the following table wherein the $LD_{50}/ED_{50}$ indices as well as the ratio of indices (index of the test compound:index of Lidocaine) are also given.

| No. of the compound with No. of the respective Example | mg/kg | | $LD_{50}ED_{50}$ index | index ratio |
|---|---|---|---|---|
| | $ED_{50}$ | $LD_{50}$ | | |
| Lidocaine | 7.7 | 25.1 | 3.26 | 1 |
| 1528 (Example 16) | 0.68 | | | |
| 1529 (Example 17c) | 0.15 | 35.2 | 234.0 | 71.8 |
| 1530 (Example 17d) | 1.8 | | | |
| 1531 (Example 17f) | 1.0 | | | |
| 1533 (Example 10) | 1.4 | | | |
| 1534 (Example 11c) | 1.1 | | | |
| 1535 (Example 11b) | 2.5 | | | |
| 1536 (Example 11a) | 1.8 | | | |
| 1537 (Example 11d) | 4.0 | | | |
| 1539 (Example 11f) | 0.25 | 64.0 | 256.0 | 78.5 |
| 1540 (Example 12) | 0.4 | | | |
| 1541 (Example 22, 6α,9β-isomer) | 3.5 | | | |
| 1542 (Example 18) | 0.43 | 21.7 | 50.5 | 15.5 |
| 1543 (Example 19) | 0.6 | | | |
| 1544 (Example 13) | 1.4 | | | |
| 1545 (Example 14) | 1.8 | | | |
| 1547 (Example 23, 6α,9β-isomer) | 0.71 | 36.3 | 51.1 | 15.7 |
| 1548 (Example 11g) | 2.5 | | | |
| 1641 (Example 17h) | 0.55 | | | |
| 1642 (Example 17i) | 0.5 | | | |
| 1643 (Example 17j) | 1.2 | | | |
| 1644 (Example 17k) | 1.4 | | | |
| 1645 (Example 17l) | 1.2 | | | |
| 1648 (Example 17m) | 1.0 | | | |
| 1658 (Example 21a) | 2.3 | | | |
| 1797 (Example 17g) | 0.45 | | | |
| 1799 (Example 17a) | 1.1 | | | |
| 1800 (Example 17b) | 0.75 | | | |
| 1801 (Example 17e) | 0.7 | | | |
| 1840 (Example 21b) | 0.95 | | | |

In the case of oral administration the new compounds were also active on aconitine arrhythmia model. In particular test compound No. 1529 showed in Wistar rats prolonged anti-arrhythmic effect in 20 mg/kg dose p.o.

The new compounds of the formula (I) showed also marked local anaesthetic activities on the ischiadic nerve isolated from frog. In this respect test compound No. 1542 was four times more favorable effective than Lidocaine, and even the compound No. 1539 which was the least effective one, was as active as the Lidocaine.

The new compounds have no beta-receptor blocking effect. In a local anaesthetic mechanism of effect the compounds of the formula (I) influence certain electrophysiological parameters of the heart. E.g. increase in conduction time and refractory period were observed on heart isolated from guinea pig. In these tests all the test compounds were superior to quinidine and compound No. 1542 was about five times more active than the quinidine was.

The prospective therapeutical dosis of the new compounds in clinical treatment is about 0.15–1.0 mg/kg under i.v. and 10 mg/kg under p.o. administration.

The invention also provides a process for the preparation of the new compounds of the formula (I), wherein $R^1$, $R^2$, $R^3$ and $R^4$, and in the definition of $R^4$ the substituents $R^5$ and $R^6$ are as defined above, as well as the stereoisomers and the pharmaceutically acceptable acid addition salts thereof, in which ($a_1$) a tetrahydropyridine derivative of the formula (V), wherein $R^1$, $R^2$ and $R^3$ are as defined above as reacted with acrolein to yield a mixture of the 6α- and 6β-isomers of the new azabicyclononan-9-one derivative of the formula (IV), in which $R^1$, $R^2$ and $R^3$ are as defined above, and the resulting mixture is optionally separated into the individual isomers and/or is subjected to reduction to yield the isomeric alcohols of the formula (I), wherein $R^4$ is a hydroxy group and $R^1$, $R^2$ and $R^3$ are as defined above and the alcohol(s) optionally after separation into the individual isomers is/are isolated, or if desired reacted with an etherifying agent of the formula (III), wherein $R^5$ is as defined above and X is a halogen, to yield a compound of the formula (I), in which $R^4$ is an etherified hydroxy group of the formula —$OR^5$ and $R^1$, $R^2$ and $R^3$ are as defined above, or with a carboxylic acid of the formula (II), or a reactive derivative thereof capable of acylation, in which $R^6$ is as defined above, to yield a compound of the formula (I), in which $R^1$, $R^2$ and $R^3$ are as defined above, and $R^4$ is an esterified hydroxy group of the formula —$OOCR^6$, and any of the compounds of the formula (I) optionally is separated into the individual isomers, and if desired converted into a pharmaceutically acceptable acid addition salt, or ($a_2$) a new azabicyclononan-9-one derivative of the formula (IV), in which $R^1$, $R^2$ and $R^3$ are as defined above, or an isomer thereof is subjected to reduction to yield the isomeric alcohols of the formula (I), wherein $R^4$ is a hydroxy group and $R^1$, $R^2$ and $R^3$ are as defined above, and the alcohol(s) optionally after separation into the individual isomers are isolated, or if desired reacted with an etherifying agent of the formula (III), wherein $R^5$ is as defined above and X is halogen, to yield a compound of the formula (I), in which $R^4$ is an etherified hydroxy group of the formula —$OR^5$, or with a carboxylic acid of the formula (II), or a reactive derivative thereof capable of acylation, in which $R^6$ is as defined above, to yield a compound of the formula (I), in which $R^4$ is an esterified hydroxy group of the formula —$OOCR^6$, and any of the compounds of the formula (I) optionally is separated into the individual isomers, and if desired converted into a pharmaceutically acceptable acid addition salt, or ($a_3$) a new alcohol of the formula (I), wherein $R^1$, $R^2$ and $R^3$ are as defined above and $R^4$ is a hydroxy group, is reacted with an etherifying agent of the formula (III), wherein $R^5$ is as defined above and X is a halogen, to yield a compound of the formula (I), in which $R^4$ is an etherified hydroxy group of the formula —$OR^5$, or with a carboxylic acid of the formula (II), or a reactive derivative thereof capable of acylation, in which $R^6$ is as defined above, to yield a compound of the formula (I), in which $R^4$ is an esterified hydroxy group of the formula —$OOCR^6$, and any of the compounds of the formula (I) optionally is separated into the individual isomers, and if desired converted into a pharmaceutically acceptable acid addition salt.

According to the invention the starting compound is a tetrahydropyridine derivative (enamine) of the formula (V), which can be prepared by reacting an amine of the formula (VII), with a piperidone derivative of the formula (VI), in a manner known per se. To promote better yields, water formed in the reaction should be removed either by the aid of a water binding agent, preferably with a molecular sieve (e.g. zeolite, such as Klinosorb-4) or by azeotropic distillation optionally carried out in the presence of a catalyst, e.g. p-toluenesulfonic acid.

According to the invention to the first reaction step an enamine of the formula (V), is reacted with acrolein yielding a new azabicyclo[3.3.1]nonan-9-one of the formula (IV). In position 6 of the resulting compound the

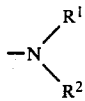

substituent may have α- or β-configuration. This isomeric mixture if desired is separated into the individual isomers, or the mixture thereof is used for the preparation of the compounds of the formula (I). The latter solution is the preferred one. If one should separate the 9-one isomers, gas-chromatography is suitable for this purpose. The α-isomer has the shorter retention time and makes up the predominant part (about 70–80%) of the mixture.

According to the invention in the second reaction step the 6α- and/or 6β-isomers of the formula (IV) are reduced. The reduction can be carried out by catalytic hydrogenation or by using a metal alcoholate or a complex metal hydride in the presence of an organic solvent. In the case of catalytic hydrogenation a platinum metal on a carrier, Raney nickel or platinum oxide can be used as catalyst in an alcohol. The preferred metal alcoholate is aluminum isopropylate in isopropanol, the preferred complex metal hydrides are alkali metal borohydrides or sodium-dihydro-bis(2-methoxyethoxy)-aluminate in an non-protic solvent.

When a mixture of the 6α- and 6β-isomers of the formula (I) is reduced, the reduction results in a mixture of four isomeric alcohols shown by the formula (Ia), (Ib), (Ic) and (Id) below.

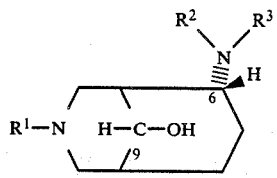
(Ia)

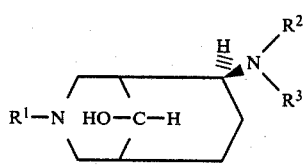
(Ib)

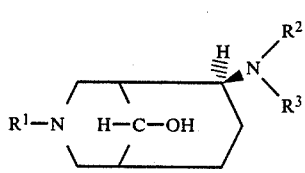
(Ic)

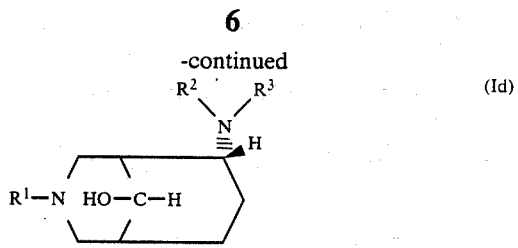
(Id)

The isomer wherein the hydroxy group (or —R4 group) in position 9 is on the side of the disubstituted amino group in position 6 is termed as 9α-isomer, whereas that in which the hydroxy group (or —R4 group) in position 9 is on the opposite side of the disubstituted amino group in position 6 is termed as 9β-isomer. Thus, formula (Ia) correspondes to the 6α,9α, formula (Ib) to the 6β,9β, formula (Ic) to the 6β,9α, and formula (Id) to the 6α,9β-isomer.

The determination of the ratio of the individual isomers in the isomeric mixture can e.g. be performed by gas-chromatography on Carbowax 20M absorbent pretreated with 2% aqueous solution of potassium hydroxide. About 70% of the mixture showed 9α-configuration, in which the amount of the 6α,9α-isomer was predominant. The remaining 30% was assigned as 9β-structure, in which only negligible amount showed 6β,9β and the predominant part showed 6α,9β-configuration.

A possible way for the separation of the isomers is crystallisation from a suitable non-protic solvent, preferably from diisopropyl-ether. On cooling most of the 6α,9α-isomer crystals and optionally can be purified by recrystallization. The mother liquors obtained at recrystallization is/are then subjected to fractional distillation when the 6β,9α-isomer distills off. The residue consists of an 1:1 mixture of the 6α,9α- and 6α,9β-isomers and a negligible amount of the 6β,9β-isomer. From them the 6α,9β-component in chloroform forms ester selectively with carboxylic acid chlorides, preferably with benzoyl chloride, 4-nitrobenzoyl chloride, xanthen-9-carbonyl chloride, or the like. The ester so obtained corresponds to a compound of the formula (I), wherein R4 is an esterified hydroxy group of the formula —OOCR6. It is isolated, or if desired is re-converted into the appropriate pure 6α,9β-ol, which if desired is converted into another ester of the formula (I). 9-ol-isomers is based on that the 6α,9α-ol isomer does not form ester with 9-nitrobenzoyl chloride or the like. Thus when the mixture of the four isomeric alcohols is acylated, the 6α,9α-ol being present in the greatest amount in the mixture remains inert, while the other three isomers become acylated. The pH of the reaction mixture is adjusted to 7.5–8.5, and then extracted with a solvent of the ether type. The phases are separated. From the aqueous layer at pH 10 the unchanged 6α,9α-ol can be with a chlorinated hydrocarbon extracted. From the organic layer after evaporation and taking up the residue, the mixture of the 6α,9β- and 6β,9α-ols is precipitated with hydrochloric acid. The precipitate is filtered off and from the filtrate after evaporation the 6β,9β-ol crystals.

All the four isomers obtained are in racemic form. If desired resolution can be performed by utilizing dibenzoyl-D-(or L)-tartaric acid.

Any of the compounds obtained above can be etherified or esterified.

When a 9-ol compound of the formula (I) is reacted with a compound of the formula (III), compounds of formula (I) in which $R^4$ is an etherified hydroxy group of the formula —$OR^5$ are obtained. The reaction is performed in a dipolar-aprotic solvent. When there is an acid binding agent in the medium directly compounds of the ether type are obtained. It is preferred, however, prior to the etherification to convert the 9-alcohol into the respective 9-alkali metal alcoholate which is then reacted with a compound of the formula (III). When a compound of the formula (I), wherein $R^4$ is an etherified hydroxy group of the formula —$OR^5$ is to be prepared in which $R_5$ is an aryl type substituent, such as an optionally substituted phenyl, benzyl or naphthyl group, it is preferred to utilize a halide of the formula (III), wherein X is a fluorine atom. After the etherification has terminated, from the reaction mixture the excess of the alkali metal hydride is decomposed and the product is by extraction and/or evaporation isolated, and if desired is converted into a pharmaceutically acceptable acid addition salt.

When a 9-ol compound of the formula (I) is reacted with a carboxylic acid of the formula (II) or a reactive derivative thereof capable of acylation, compounds of the formula (I), wherein $R^4$ is an esterified hydroxy of the formula—$OOCR^6$ are obtained. As reactive derivatives carboxylic acid halides and reactive esters can be taken into consideration. In the latter case trans-esterification takes place.

The acylation is performed in a suitable organic solvent. When an ester, preferably a $C_{1-5}$ aliphatic ester of the carboxylic acid of the formula (II) is used as acylating agent, it is preferred to use a catalyst to promote trans-esterification. The acylation reaction in chloroform is selective: in this medium the $6\alpha,9\alpha$-ol remains inert to esterification, while the other components of the isomeric mixture become acylated. This experience was utilized at the separation of the isomeric mixture.

The product of the acylation is isolated in a manner known per se, and if desired converted into a pharmaceutically acceptable acid addition salt thereof.

SPECIFIC EXAMPLES

The invention is elucidated in detail by the aid of the following non-limiting Examples.

EXAMPLE 1

To a solution of 193 g of freshly distilled 1-methyl-4-dimethylamino-1,2,5,6-tetrahydropyridine in 300 ml dioxane a solution of 77 g of acrolein in 300 ml of dioxane is added dropwise under stirring at 0°–5° C. within 5 hours. The reaction mixture is left to stand at ambient temperature overnight. Then the dioxane is distilled off and thereafter the residue is purified by vacuum distillation. A light yellow oil is obtained with a yield of 74.7%, bp.: 80°–100° C./10 Pa., consisting of 70–80% of 6α- and 20–30% of 6β-dimethylamino-3-methyl-3-azabicyclo[3.3.1]nonan-9-one [a mixture of the stereoisomers of the formula (IV)].

The respective starting substance of the formula (V) can be prepared as follows:

To 1000 g of Klinosorb-4 molecular sieve 500 ml of dry ether and 226 g of 1-methyl-4-piperidone are added and thereafter dimethylamine gas is bubbled into the reaction mixture with a rate allowing only slow reflux of the mixture in the initial period of the reaction. The dimethylamine gas is introduced into the reaction medium for 8 hours on three subsequent days, thereafter the mixture is filtered, the Klinosorb is washed with ether and the combined etheral solution is evaporated to dryness under reduced pressure. The oily residue is purified by distillation in vacum to yield 70% of 1-methyl-4-dimethylamino-1,2,5,6-tetrahydropyridine; bp.: 78°–82° C./2.66 kPa.

EXAMPLE 2

Freshly distilled 1-ethyl-4-dimethylamino-1,2,5,6-tetrahydropyridine is reacted with acrolein as described in Example 1 to give a colourless oil consisting of 80% of 6α- and 20% of 6β-dimethylamino-3-ethyl-3-azabicyclo[3.3.1]nonan-9-one with a yield of 48.8%, bp.: 90°–95° C./2.6 Pa; $n_D^{20}$=1.4980.

The respective starting substance is prepared from 90 g of 1-ethyl-4-piperidone with dimethylamine gas introduced into the reaction mixture on three subsequent days for a total 20 hours introduction time as described in Example 1, 1-ethyl-4-dimethylamino-1,2,5,6-tetrahydropyridine is obtained with a yield of 73.5%, bp.: 90°–93° C./1.47 kPa; $n_D^{20}$=1.4931.

EXAMPLE 3

1-Butyl-4-piperidone is reacted with dimethylamine gas as described in Example 1, affording 1-butyl-4-dimethylamino-1,2,5,6-tetrahydropyridine with a yield of 77.9%, bp.: 103°–106° C./1.5 kPa. The tetrahydropyridine derivative so obtained is freshly distilled and reacted with acrolein as described in Example 1, to give a light yellow oil with a yield of 44.2%, consisting of 75% of 6α-, and 25% of 6β-dimethylamino-3-butyl-3-azabicyclo[3.3.1]nonan-9-one, bp.: 110°–116° C./7 Pa; $n_D^{20}$=1.4933.

EXAMPLE 4

Freshly distilled 1-methyl-4-diethylamino-1,2,5,6-tetrahydropyridine is reacted with acrolein to give a mixture of 80% of 6α-diethylamino-3-methyl-3-azabicyclo[3.3.1]nonan-9-one and 20% of 6β-isomer thereof, with a yield of 26.4%, bp.: 95°–108° C./13.3 Pa; $n_D^{20}$=1.4987.

The starting substance is prepared as follows: To 1000 g of Klinosorb-4 molecular sieve 1000 ml of dry diethyl ether, 226 g of 1-methyl-4-piperidone and 219 g of dry diethylamine are added. The reaction mixture is kept at room temperature for 4 days and then filtered off. The Klinosorb-4 is washed with ether, the filtrate and the washing are combined, the solvent is distilled off and the residue is purified by distillation in vacuo to give 1-methyl-4-diethylamino-1,2,5,6-tetrahydropyridine with a yield of 59.9%, bp.: 88°–106° C./1.5 kPa; $n_D^{20}$=1.4825.

EXAMPLE 5

Freshly distilled 1-methyl-4-dibutylamino-1,2,5,6-tetrahydropyridine is reacted with acrolein as described in Example 1, to give a mixture of isomers consisting of 80% of 6α-, and 20% of 6β-dibutylamino-3-methyl-3-azabicyclo-[3.3.1]nonan-9-one with a yield of 40.6%, bp.: 108°–112° C./10 Pa; $n_D^{25}$=1.4850.

The respective starting substance is prepared as follows:

To a mixture of 800 ml of toluene, 226 g of 1-methyl-4-piperidone and 310.2 g dibutylamine 0.5 g of 4-toluenesulfonic acid is added. The mixture is refluxed for about 8 hours in a flask equipped with a water separator.

Then the solvent is distilled off and the residue is purified by distillation in vacuo to give 1-methyl-4-dibutylamino-1,2,5,6-tetrahydropyridine with a yield of 50.1%; bp.: 130°–138° C./1.73 kPa; $n_D^{25}$=1.480.

EXAMPLE 6

240 g of a 75:25 mixture of 6α- and 6β-dimethylamino-3-methyl-3-azabicyclo[3.3.1]nonan-9-one is taken up in 600 ml of dry ether, and to the resultant mixture 233 g of 70% sodium-dihydro-bis(2-methoxyethoxy)aluminate dissolved in 100 ml dry ether is added dropwise at about 15° C. over 3 hours. Following this period, 500 ml of 20% sodium hydroxide aqueous solution is added, the phases are separated and the aqueous layer is extracted twice with 100 ml. portions of ether. The etheral solutions are combined, dried over magnesium sulfate and concentrated. The residue is dissolved in 300 ml of warm diisopropylether, from which on cooling a crystalline mixture of 6α-dimethylamino-3-methyl-3-azabicyclo[3.3.1]nonane-9α-ol and the corresponding 6α,9β-ol is obtained.

The product is recrystallized twice from an about 4fold amount of diisopropyl ether affording selectively the 6α-dimethylamino-3-methyl-3-azobicyclo[3.3.1]nonane-9α-ol free of the 99β-ol isomer; mp.: 119° C.

The conformation was confirmed by $^1$H-NMR data obtained by the aid of Eu(fod)$_3$ shift reagent. The Eu(fod)$_3$ abbreviation is given for tris(6,6,7,7,8,8,8-heptafluoro-2,2-dimethyl-3,5-octanediol)-europium.

$^1$H-NMR (CDCl$_3$): δ 3.8 ppm, t, C(9)—H; 2.19 ppm, s, C(6) N(CH$_3$)$_2$; 2.07 ppm, s, N(3) CH$_3$; 3.25–1.5 ppm, m, CH, CH$_2$.

EXAMPLE 7

From the mother liquor of the first recrystallization of the 9-ol isomeric mixture described in Example 6, the 6β-dimethylamino-3-methyl-3-azabicyclo[3.3.1]nonane-9-ol can be obtained. The said mother liquor is concentrated and the residue is subjected to fractional distillation utilizing a column with wire gauze bed to yield 6β-dimethylamino-3-methyl-3-azabicyclo[3.3.1]nonane-9α-ol, bp,: 74°–75° C./2.7 Pa. On cooling the product needles with mp. 37°–40° C. The conformation was assigned by $^1$H-NMR taken by the aid of Eu(fod)$_3$ shift reagent.

$^1$H-NMR (CDCl$_3$) δ: 3.61 ppm, t, C(9)-H; 2.27 ppm, s, C(6)N(CH$_3$)$_2$; 2.07 ppm, s, N(3)CH$_3$; 3.09–1.25 ppm, m, CH, CH$_2$.

EXAMPLE 8

The 6α-dimethylamino-3-methyl-3-azabicyclo[3.3.1]nonane-9β-ol can be prepared free of the other isomers from its benzoyl ester prepared according to Example 22.

4 g of 6α-dimethylamino-3-methyl-9β-benzoyloxy-3-azabicyclo[3.3.1]nonane dihydrochloride is dissolved in 25 ml of ethanol, and to the solution 20 ml of 25% sodium hydroxide aqueous solution is added. The reaction mixture is left to stand at ambient temperature for 3 hours, then the alcohol is removed, the residue is saturated with potassium carbonate and is extracted three times with 30 ml. portions of chloroform. The combined extracts are dried over magnesium sulfate and concentrated. The crystalline residue after sublimation in vacou melts at 111° C. Yield: 94.7% 6α-dimethylamino-3-methyl-3-azabicyclo[3.3.1]nonane-9β-ol.

The dihydrochloride of the base melts at 256° C. under decomposition after recrystallization from ethanol. The structure was assigned by $^1$H-NMR taken with the aid of Eu(fod)$_3$ shift reagent.

$^1$H-NMR (CDCl$_3$): δ 3.46 ppm, t, C(9)—H; 2.19 ppm, s, C(6)N(CH$_3$)$_2$; 2.09 ppm, s, N(3)—CH$_3$; 2.81–1.5 ppm, m, CH, CH$_2$.

EXAMPLE 9

The 6β-dimethylamino-3-methyl-3-azabicyclo[3.3.1]nonane-9β-ol can be prepared in pure, isomer-free state from its 4-nitrobenzoyl ester prepared according to Example 24.

4 g of 6β-dimethylamino-3-methyl-9β-(4'-nitrobenzoyloxy)-3-azabicyclo[3.3.1]nonane dihydrochloride is dissolved in 20 ml of water, and to the solution 5.6 g of potassium hydroxide and 15 ml of ethanol are added. The reaction mixture is left to stand for 1 hour, the alcohol is removed and is extracted three times with 30 ml. portions of chloroform. The organic phase is dried over magnesium sulfate and concentrated to give the 6β,9β-ol as a colorless, dense oil with a yield of 96%, $n_D^{20}$ = 1.5125.

The dihydrochloride of the base melts at 286°–288° C. uner decomposition after recrystallization from ethanol.

The conformation of the isomer was assigned by $^1$H-NMR taken by the aid of Eu(fod)$_3$ shift reagent.

$^1$H-NMR (CDCl$_3$): δ 3.92 ppm, t, C(9)—H; 2.17 ppm, s, C(6)N(CH$_3$), 2.11 ppm, s, N(3)CH$_3$; 2.81–1.35 ppm, m, CH, CH$_2$.

EXAMPLE 10

9.0 g of 6α-dimethylamino-3-methyl-3-azabicyclo[3.3.1]nonane-9α-ol is dissolved in 100 ml of dry dimethylformamide and to the resultant solution 2.4 g of sodium hydride are added under nitrogen atmosphere. When the spontaneous hydrogen evaluation subsides the reaction mixture is stirred at 60° C. for 30 minutes and then 11.0 g of fluorobenzene are added to the mixture in one portion. The mixture is maintained at 60°–100° C. for some hours. When the reaction has terminated, the mixture is diluted with 20 ml of ethanol to decompose the excess of the sodium hydride, then is acidified with 15 ml of concentrated hydrochloric acid and is evaporated to dryness in vacuo. The residue is dissolved in 550 ml of water and extracted twice with 50 ml. portions of ether. To the aqueous layer potassium carbonate is added until an oily phase separates, which is extracted three times with 50 ml. portions of ether. The combined etheral extracts are dried over magnesium sulfate, filtered, and the filtrate is evaporated. The residue is purified by distillation in vacuo affording 6α-dimethylamino-3-methyl-9α-phenoxy-3-azabicyclo[3.3.1]nonane with a yield of 84.2%; bp.: 107° C./2.7 Pa. $n_D^{25}$ = 1.5408.

The fumarate of the base melts at 161°–162° C. under slight decomposition after recrystallization from ethanol.

EXAMPLE 11

1 molar equivalent of 6α-dimethylamino-3-methyl-3-azabicyclo[3.3.1]nonane-9α-ol is reacted with 1.5 molar equivalents of the respective aryl fluoride as described in Example 10 to yield the compounds listed below:

(a) 6α-dimethylamino-3-methyl-9α-(2'-chlorophenoxy)-3-azabicyclo[3.3.1]nonane dihydrochloride, yield: 93.6%; melts at 247°–249° C. under decomposition, after recrystallization from a mixture of ethanol, acetone and ether.

(b) 6α-dimethylamino-3-methyl-9α-(3'-chlorophenoxy)-3-azabicyclo[3.3.1]nonane monohydrochloride, yield: 82.9%, melts at 165°–167° C. under decomposition after recrystallization from ethanol-ether.

(c) 6α-dimethylamino-3-methyl-9α-(4'-chlorophenoxy)-3-azabicyclo[3.3.1]nonane fumarate, yield: 94.7%, melts at 172°–173° C. under slight decomposition after recrystallization from ethanol-acetone.

(d) 6α-dimethylamino-3-methyl-9α-(3',4'-dichlorophenoxy)-3-azabicyclo[3.3.1]noname fumarate, yield: 99%, melts at 171°–172° C. under slight decomposition, after recrystallization from ethanol. The respective base melts at 87°–88° C. after recrystallization from diisopropyl ether—hexane.

(e) 6α-dimethylamino-3-methyl-9α-(2',4'-dibromophenoxy)-3-azabicyclo[3.3.1]nonane dihydrochloride, yield: 86.9%; sinters at 130° C., effervescence at 136° C.

(f) 6α-dimethylamino-3-methyl-9α-(3'-trifluoromethylphenoxy)-3-azabicyclo[3.3.1]nonane fumarate, yield: 81.3%, mp.: 158°–159° C. (decomposition) after recrystallization from ethanol and ether. The respective base is a colorless oil, bp.: 115° C./2.7 Pa; $n_D^{25} = 1.5021$.

(g) 6α-dimethylamino-3-methyl-9α-(4'-methylphenoxy)-3-azabicyclo[3.3.1]nonane fumarate; yield: 43.1%, crystals from a mixture of ethanol, acetone and ether, mp.: 157°–159° C. (decomposition).

(h) 6α-dimethylamino-3-methyl-9α-(4'-phenylphenoxy)-3-azabicyclo[3.3.1]nonane dihydrochloride, yield: 93.7%, crystals from ethanol, mp: 260° C. (decomposition). The respective base crystals from acetone, mp.: 91° C.

EXAMPLE 12

9.0 g of 6α-dimethylamino-3-methyl-3-azabicyclo[3.3.1]nonane-9α-ol is reacted with 24.7 g of benzhydryl bromide as described in Example 10, to give 6α-dimethylamino-3-methyl-9α-benzhydryloxy-3-azabiocyclo[3.3.1]nonane which is converted into the fumarate salt. Yield: 41.7%. Mp.: 160°–161° C. with decomposition, after recrystallization from ethanol.

EXAMPLE 13

7.0 g of 6β-dimethylamino-3-methyl-3-azabicyclo[3.3.1]nonane-9α-ol in 50 ml of dru dimethylformamide is reacted with 10.0 g of fluorobenzene as described in Example 10 to give 6β-dimethylamino-3-methyl-9α-phenoxy-3-azabicyclo-[3.3.1]nonane. The product is converted into the dihydrochloride salt with hydrogen chloride dissolved in dry ether. Yield: 72.6%, m.p.: 287° C. (decomposition), after recrystallization from methanol.

EXAMPLE 14

By using 6β-dimethylamino-3-methyl-3-azabicyclo[3.3.1]nonane-9α-ol as starting material and following the method described in Example 10, 6β-dimethylamino-3-methyl-9α-(3'-trifluoromethylphenoxy)-3-azabicyclo[3.3.1]nonane dihydrochloride is prepared. Yield: 77.1%, m.p.: 265° C. (decoposition), after recrystallization from ethanol.

EXAMPLE 15

5 g of 6β-dimethylamino-3-methyl-3-azabicyclo[3.3.1]nonane-9α-ol is reacted with 10 g of benzhydryl bromide as described in Example 10, and the product is converted into the dihydrochloride salt and is recrystallized from ethanol to yield 6β-dimethylamino-3-methyl-9α-(benzhydryloxy)-3-azabicyclo[3.3.1]nonane dihydrochloride. Yield: 78.3%, m.p.: 237°–238° C. (decomposition).

EXAMPLE 16

7 g of 6α-dimethylamino-3-methyl-3-azabicyclo[3.3.1]nonane-9α-ol is dissolved in 50 ml of dry pyridine. To the resultant solution 8 g of benzoyl chloride in 50 ml of dry pyridine is added dropwise at 5°–10° C. within 20 minutes with stirring. The reaction mixture is stirred for 1–3 hours at room temperature and thereafter the pyridine is distilled off. The residue is extracted with 50 ml of ether. The aqueous layer is rendered alkaline with potassium carbonate and is extracted three times with 50 ml. portions of chloroform. The extracts are combined, dried over magnesium sulfate, filtered, and the filtrate is evaporated to dryness. To the residue hydrogen chloride dissolved in ether is added to afford the 6α-dimethylamino-3-methyl-9α-benzoyloxy-3-azabicyclo[3.3.1]nonane dihydrochloride with a yield of 92.8%. The product crystals from methanol, sinters at 160° C., melts at 166°–168° C. with decomposition.

EXAMPLE 17

By using 6α-dimethylamino-3-methyl-3-azabicyclo[3.3.1]nonane-9α-ol as starting substance and different carboxylic acid halides as reactant the following compounds were prepared.

(a) By using 4-methylbenzoylchloride as reactant 6α-dimethylamino-3-methyl-9α-(4'-methylbenzoyloxy)-3-azabicyclo[3.3.1]nonane dihydrochloride was obtained with a yield of 62.9%. Crystals from ethanol, melts at 153°–155° C. with decomposition. The respective base melts at 65°–67° C.

(b) By using 4-chlorobenzoyl chloride as reactant 6α-dimethylamino-3-methyl-9α-(4'-chlorobenzoyloxy)-3-azabicyclo[3.3.1]nonane dihydrochloride was prepared with a yield of 24.4%. Crystals from ethanol, melts at 192°–194° C. with decomposition.

(c) By using 3,4,5-trimethoxybenzoyl chloride as reactant, 6α-dimethylamino-3-methyl-9α(3',4',5'-trimethoxybenzoyloxy)-3-azabicyclo[3.3.1]nonane was obtained with a yield of 66.4%. Crystals from n-butanol, melts at 122°–123° C. The appropriate dihydrochloride crystals from ethanol, melts at 180°–184° C. with decomposition.

(d) By using 4-phenylbenzoyl chloride as reactant, 6α-dimethylamino-3-methyl-9α-(4'-phenylbenzoyloxy)-3-azabicyclo[3.3.1]nonane is obtained with a yield of 72.2%; crystals from diisopropyl ether, melts at 122°–124° C. The dihydrochloride after recrystallization from ethanol melts at 252°–253° C. with decomposition.

(e) By using 2-naphthoyl chloride as reactant, 6α-dimethylamino-3-methyl-9α-(2'-naphthoyloxy)-3-azabicyclo[3.3.1]nonane is obtained with a yield of 82.3%. The product crystals from acetone, melts at 128°–130° C. with decomposition after recrystallization from diethylene glycol monomethyl ether.

(f) By using 9-xanthen carbonyl chloride as reactant 6α-dimethylamino-3-methyl-9α-(xanthen-9-carbonyloxy)-3-azabicyclo[3.3.1]nonane dihydrochloride is obtained with a yield of 72.7%; crystals from isopropanol, melts at 211°–215° C.

(g) By using 2-thenoyl chloride as reactant 6α-dimethylamino-3-methyl-9α-(2'-thenoyloxy)-3-azabicyclo[3.3.1]nonane is obtained which melts at 81°–83° C. The dihydrochloride after recrystallization from ethanol effervesces at 190° C., melts at 206°–208° C. with decomposition. Yield: 93.1%.

(h) By using 4-fluorobenzoyl chloride as reactant 6α-dimethylamino-3-methyl-9α-(4'-fluorobenzoyloxy)-3-azabicyclo[3.3.1]nonane dihydrochloride monohydrate is obtained with a yield of 51.5%. Crystals from aqueous ethanol, melts at 255°–257° C. with decomposition.

(i) By using 3-fluorobenzoyl chloride as reactant 6α-dimethylamino-3-methyl-9α-(3'-fluorobenzoyloxy)-3-azabicyclo[3.3.1]nonane dihydrochloride is obtained with a yield of 67.8%. Crystals from aqueous methanol, melts at 180°–184° C. with decomposition.

(j) By using 3,4-dichlorobenzoyl chloride as reactant 6α-dimethylamino-3-methyl-9α-(3',4'-dichlorobenzoyloxy)-3-azabicyclo[3.3.1]nonane dihydrochloride is obtained with a yield of 94.4%. Crystals from aqueous methanol, melts at 266°–267° C. with decomposition. The respective base melts at 99–100 (ethanol).

(k) By using 2-chlorobenzoyl chloride as reactant 6α-dimethylamino-3-methyl-9α-(2'-chlorobenzoyloxy)-3-azabicyclo[3.3.1]nonane dihydrochloride monohydrate is obtained with a yield of 68.6%. Crystals from aqueous methanol, melts at 170°–175° C. with decomposition.

(l) By using 3-chlorobenzoyl chloride as reactant 6α-dimethylamino-3-methyl-9α-(3'-chlorobenzoyloxy)-3-azabicyclo[3.3.1]nonane dihydrochloride monohydrate is obtained with a yield of 77%. Crystals from aqueous methanol, melts at 175°–177° C. with decomposition.

(m) By using 3-trifluoromethylbenzoyl chloride as reactant 6α-dimethylamino-3-methyl-9α-(3'-trifluoremethylbenzoyloxy)-3-azabicyclo[3.3.1]nonane dihydrochloride is obtained with a yield of 90%. Crystals from aqueous ethanol, melts at 169°–172° C. with decomposition. The respective base crystals from hexane and melts at 97°–98° C.

(n) By using cinnamoyl chloride as reactant 6α-dimethylamino-3-methyl-9α-cinnamoyloxy-3-azabicyclo[3.3.1]nonane dihydrochloride is obtained with a yield of 79.7%. Crystals from ethanol, melts at 196°–201° C. with decomposition.

(o) By using 4-chlorocinnamoyl chloride as reactant 6α-dimethylamino-3-methyl-9α-(4'-chlorocinnamoyloxy)-3-azabicyclo[3.3.1]nonane dihydrobromide is obtained with a yield of 68.6%. Crystals from methanol, melts at 226°–229° C. with decomposition.

(p) By using 3,4,5-trimethoxycinnamoyl chloride as reactant 6α-dimethylamino-3-methyl-9α-(3',4',5'-trimethoxycinnamoyloxy)-3-azabicyclo[3.3.1]nonane dihydrochloride is obtained with a yield of 28.5%. Crystals from ethanol, melts at 223°–225° C. with decomposition.

(q) By using 1-naphthoyl chloride as reactant 6α-dimethylamino-3-methyl-9α-(1'-naphthoyloxy)-3-azabicyclo[3.3.1]nonane dihydrochloride is obtained with a yield of 64.9%. Crystals from methanol, melts at 195°–198° C. with decomposition.

(r) By using 6-chloro-2-naphthoyl chloride as reactant, 6α-dimethylamino-3-methyl-9α-(6'-chloro-2'-naphthoyloxy)-3-azabicyclo[3.3.1]nonane dihydrochloride is obtained with a yield of 94.5%. Crystals from methanol, melts at 254°–257° C. with decomposition.

(s) By using 1,2,3,4-tetrahydro-2-naphthoyl chloride as reactant 6α-dimethylamino-3-methyl-9α-(1',2',3',4'-tetrahydro-2'-naphthoyloxy)-3-azabicyclo[3.3.1]nonane dihydrochloride is obtained with a yield of 92.2%. Crystals from ethanol, melts at 160°–170° C. with decomposition.

(t) By using phenoxyacetyl chloride as reactant, 6α-dimethylamino-3-methyl-9α-(phenoxyacetyloxy)-3-azabicyclo[3.3.1]nonane dihydrobromide is obtained with a yield of 75%. Crystals from methanol, melts at 257°–259° C. with decomposition.

EXAMPLE 18

7.0 g of 6β-dimethylamino-3-methyl-3-azabicyclo[3.3.1]nonane-9α-ol dissolved in 50 ml of dry pyridine is reacted with 8 g of benzoyl chloride in 50 ml dry pyridine as described in Example 16 to give 6β-dimethylamino-3-methyl-9α-benzoyloxy-3-azabicyclo[3.3.1]nonane which is then converted into the dihydrochloride salt in a manner known per se. The salt crystals from a mixture of methanol and water, melts at 300° C. with decomposition. Yield: 86.8%.

EXAMPLE 19

By reacting 6β-dimethylamino-3-methyl-3-azabicyclo[3.3.1]nonane-9α-ol with xanthen-9-carbonyl chloride as described in Example 16 6β-dimethylamino-3-methyl-9α-(xanthen-9'-carbonyloxy)-3-azabicyclo[3.3.1]nonane is obtained. Its dihydrochloride crystals from methanol, melts at 195° C. with decomposition. Yield=85.5%.

EXAMPLE 20

5 g of 6β-dimethylamino-3-methyl-3-azabicyclo[3.3.1]nonane-9α-ol is dissolved in 50 ml of chloroform. The solution is maintained at a temperature not higher then 20° C. and 4.7 g of 4-methylbenzoyl chloride dissolved in 10 ml of chloroform is added. The reaction mixture is allowed to stand at room temperature over 1 hour. Then the chloroform is removed in vacuo, the residue is taken up with 50 ml of water, acidified with 5 ml of concentrated aqueous hydrochloric acid and extracted twice with 50 ml. portions of diethyl ether to remove the non-basic impurities. The aqueous layer is rendered alkaline with potassium carbonate and the liberated base is extracted three times with 50 ml. portions of dichloromethane. The extracts are combined, dried over magnesium sulfate, filtered and the filtrate is evaporated to dryness. The residue is converted into the dihydrochloride salt by the aid of hydrogen chloride in ether to afford 6β-dimethylamino-3-methyl-9α-(4'-methylbenzoyloxy)-3-azabicyclo[3.3.1]nonane dihydrochloride with a yield of 83.1%. The product crystals from methanol, melts at 286° C. with decomposition.

EXAMPLE 21

By using 6β-dimethylamino-3-methyl-3-azabicyclo[3.3.1]nonane-9α-ol as starting substance and different carboxylic acid halides as reactant the following compounds were prepared:

(a) By using 4-chlorobenzoyl chloride as reactant 6β-dimethylamino-3-methyl-9α-(4'-chlorobenzoyloxy)-3-azabicyclo[3.3.1]nonane dihydrochloride was obtained with a yield of 66%. Crystals from methanol, melts at 291°–292° C. with decomposition.

(b) By using 2-naphthoyl chloride as reactant 6β-dimethylamino-3-methyl-9α-(2'naphthoyloxy)-3-azabicyclo[3.3.1]nonane dihydrochloride was obtained with a yield of 88.2%. Crystals from a mixture of methanol and water, melts at 294° C. with decomposition.

EXAMPLE 22

14 g of an about 1:1 mixture of 6α-dimethylamino-3-methyl-3-azabicyclo[3.3.1]nonane-9α-ol and 6α-dimethylamino-3-methyl-3-azabicyclo[3.3.1]nonane-9β-ol is dissolved in 100 ml of chloroform and to this solution at a temperature not higher than 20° C. 12 g of benzoylchloride is added. The mixture is allowed to stand at ambient temperature overnight. Then the chloroform is removed in vacuo, the residue is taken up in 100 ml of water, acidified with 20 ml of concentrated hydrochloric acid and extracted twice with 50 ml. portions of ether to remove the non-basic impurities. To the aqueous layer potassium carbonate is added to adjust the pH to 8 and the liberated base is extracted three times with 50 ml. portions of chloroform. The aqueous layer contains the unchanged 6α-dimethylamino-3-methyl-3-azabicyclo[3.3.1]nonane-9α-ol, while the chloroform extract contains the 6α,9β-ester. The chloroform extracts are combined, dried over magnesium sulfate, filtered and the filtrate is evaporated. The residue is converted into the dihydrochloride salt to give selectively the 6α-dimethylamino-3-methyl-9β-benzoyloxy-3-azabicyclo[3.3.1]nonane dihydrochloride. Crystals from ethanol, melts at 144°–146° C. with decomposition.

EXAMPLE 23

An about 1:1 mixture of 6α-dimethylamino-3-methyl-3-azabicyclo[3.3.1]nonane-9α-ol and 6α-dimethylamino-3-methyl-3-azabicyclo[3.3.1]nonane-9β-ol is reacted with xanthen-9-carbonyl chloride as described in Example 22. 6α-dimethylamino-3-methyl-9β-(xanthen-9'-carbonyloxy)-3-azabicyclo[3.3.1]nonane is obtained with a yield of 91.6%, crystals from diisopropyl ether, melts at 132°–133° C. Its dihydrochloride crystals from methanol and melts at 284° C. with decomposition.

EXAMPLE 24

To 145 g of an about 80:20 mixture of 6α-dimethylamino-3-methyl-3-azabicyclo[3.3.1]nonan-9-one and 6β-dimethylamino-3-methyl-3-azabicyclo[3.3.1]nonan-9-one 250 ml of ethanol and 0.7 g of PtO₂.H₂O catalyst are added. The mixture is hydrogenated under 7.6 MPa starting pressure at 80° C. until the calculated amount of hydrogen is taken up (about 3 hours). The catalyst is removed by filtration, the filtrate is evaporated to yield a colorless oil being the mixture of four isomeric alcohols (144 g).

The isomeric mixture is dissolved in 900 ml of chloroform and to the solution under cooling 133 g of benzoyl chloride dissolved in 700 ml of chloroform is added dropwise at a temperature not higher than 15° C. The reaction mixture is allowed to stand at room temperature over 3 days, then is evaporated to dryness in vacuo and the residue is extracted three times with 100 ml. portions of 10% aqueous hydrochloric acid. The pH of the solution is adjusted to 8 with potassium carbonate and thereafter is extracted three times with 100 ml. portions of ether. The extracts are combined, dried over magnesium sulfate and filtered. From the filtrate the solvent is removed, the resulting light brown oil is dissolved in 500 ml of methanol and is acidified with hydrogen chloride dissolved in dry ethanol. Upon standing a mixture of the 6α,9β and 6β,9α 4-nitrobenzoyl esters precipitates and is isolated by filtration. The filtrate is evaporated to dryness, dissolved in 300 ml of ethanol and allowed to stand overnight at 0°–10° C. The precipitate is filtered (9.1 g) dried to yield 6β-dimethylamino-3-methyl-9β-(4'-nitrobenzoyloxy)-3-azabicyclo[3.3.1]nonane dihydrochloride which melts at 297°–298° C. with decomposition after recrystallization from aqueous methanol.

EXAMPLE 25

7 g of 6α-dimethylamino-3-methyl-3-azabicyclo[3.3.1]nonane-9α-ol is mixed with 20 g of benzylic acid ethyl ester and to this mixture 0.2 g of sodium metal is added in small portions. Thereafter the reaction mixture is maintained at 90°–100° C. under 6–10 Pa pressure over 13 hours. Then the vacuum is terminated, 50 ml of 10% hydrochloric acid aqueous solution is added and the excess of the benzylic acid ethyl ester is extracted twice with 50 ml. portions of ether. The phases are separated. The aqueous layer is rendered alkaline with potassium carbonate whereupon the ester forms a separate phase which is extracted 3 times with 50 ml. portions of chloroform. The chloroform extracts were combined, dried over magnesium sulfate, filtered and the filtrate is evaporated. The residue is recrystallized from heptane affording 6α-dimethylamino-3-methyl-9α-benzyloyloxy-3-azabicyclo[3.3.1]nonane with a yield of 86%. Mp.: 115° C. The corresponding dihydrochloride salt melts at 245°–247° C. with decomposition after recrystallization from a mixture of methanol and water.

EXAMPLE 26

39 g of an about 80:20 mixture of 6α-diethylamino-3-methyl-3-azabicyclo[3.3.1]nonan-9-one and 6β-diethylamino-3-methyl-3-azabicyclo[3.3.1]nonan-9-one obtained according to Example 4 is mixed with 200 ml of isopropanol containing 35 g of aluminum-isopropylate. The reaction mixture is subjected to distillation by using a Vigreux column of 50 cm height. The distillation is carried out with 5 drops/minute rate over 3.5 hours, then is refluxed for half an hour and is again distilled slowly for half an hour. Thereafter the mixture is evaporated in vacuo, to the residue 100 ml of 30% sodium hydroxyde aqueous solution is added and then extracted four times with 50 ml. portions of dichloromethane. The extracts are combined, dried over magnesium sulfate and then the solvent is removed in vacuo. The residue, a pale yellow viscous oil is an approximatively 1:1 mixture of 6α-diethylamino-3-methyl-3-azabicyclo[3.3.1]nonane-9α-ol and 6α-diethylamino-3-methyl-3-azabicyclo[3.3.1]nonane-9β-ol. Yield: 81%, bp.: 107°–110° C./4 Pa.

EXAMPLE 27

30 g of the 1:1 mixture of 6α,9α and 6α,9β alcohols obtained according to Example 26, is dissolved in 300 ml of chloroform and under water cooling 18.65 g of benzoyl chloride is added to the solution. The reaction mixture is allowed to stand at room temperature for 24 hours and then is evaporated. The residue is dissolved in 300 ml of water. The pH is adjusted to 3 with concentrated hydrochloric acid and then extracted three times with 100 ml. portions of ether to remove the non-basic impurities. The aqueous layer is rendered alkaline with potassium carbonate (pH 8) and is extracted three times with 100 ml. portions of dichloromethane. The extracts containing the 6α,9β-ester are combined and put aside for isolation of the ester.

The pH of the aqueous layer is adjusted to 10 with a further amount of potassium carbonate and is extracted three times with 100 ml. portions of dichloromethane. The combined extracts are dried over magnesium sulfate and then the solvent is removed in vacuo. The residue, a dense oil crystals upon standing to afford 6α-diethylamino-3-methyl-3-azabicyclo[3.3.1]nonane-9α-ol with a yield of 82%. Mp.: 72% after recrystallization from heptane followed by a vacuum sublimation step.

The structure of the product was assigned by $^{13}$C-NMr and 1H-NMR from which the data of the latter one are as follows:

$^1$H-NMR (CDCl$_3$): δ C(6)N(CH$_2$CH$_3$)$_2$, t, 0.93 ppm; C(6)N(CH$_2$CH$_3$)$_2$, q, 2.59 ppm; N(3)—CH$_3$, s, 2.04 ppm; C(9)—H, t, 3.78 ppm.

EXAMPLE 28

The combined dichloromethane extract obtained at pH 8 as described in Example 27, is dried over magnesium sulfate and then the solvent is distilled off in vacuo. The residue, a viscous oil is converted into the dihydrobromide and is recrystallized from methanol to give 6α-diethylamino-3-methyl-9β-benzoyloxy-3-azabicyclo[3.3.1]nonane dihydrobromide with a yield of 80%. Mp.: 245°–246° C. (decomposition).

EXAMPLE 29

4 g of 6α-diethylamino-3-methyl-3-azabicyclo[3.3.1]nonane-9α-ol is dissolved in 50 ml of dry pyridine and to the resultant solution 3.1 g of cyclohexanoyl chloride is added below 15° C. within 10 minutes. The reaction mixture is allowed to stand at room temperature for an hour and then the most part of the pyridine is distilled off in vacuo. The residue is dissolved in 50 ml of water and is extracted with 50 ml of ether to remove the non-basic impurities.

The aqueous layer is rendered alkaline with potassium carbonate and is extracted three times with 50 ml portions of dichloromethane. The extracts are combined, dried over magnesium sulfate, filtered and the filtrate is evaporated. The residue is converted into the dihydrobromide salt to afford 6α-diethylamino-3-methyl-9α-cyclohexanoyloxy-3-azabicyclo[3.3.1]nonane dihydrobromide with a yield of 92.5%. The product crystals from ethanol, melts at 242°–244° C. with decomposition.

EXAMPLE 30

30 g of an about 80:20 mixture of 6α-dimethylamino-3-ethyl-3-azabicyclo[3.3.1]nonan-9-one and 6β-dimethylamino-3-ethyl-3-azabicyclo[3.3.1]nonan-9-one obtained according to Example 2, is dissolved in 100 ml of dry ether. To the resultant solution 27 g of 70% sodium-dihydro-bis(2-methoxyethoxy)-aluminate dissolved in 50 ml of dry ether is added dropwise below 15° C. about over 1 hour. The reaction mixture is treated with 70 ml of 20% sodium hydroxide aqueous solution, the phases are separated, and the aqueous layer is extracted twice with 50 ml. portions of ether. The extracts are combined with the separated organic phase, dried over magnesium sulfate and the solvent is removed by destillation. The residue, a viscous oil is dissolved in 50 ml of warm diisopropyl ether. On cooling crystalline 6α-dimethylamino-3-ethyl-3-azabicyclo[3.3.1]nonane-9α-ol is obtained. Mp.: 88° C. after recrystallisation from diisopropyl ether and subsequent vacuum sublimation.

The structure of the product was assigned by $^{13}$C-NMR and $^1$H-NMR from which the latter data are as follows:

$^1$H-NMR (CDCl$_3$): δ N(3)—CH$_2$—CH$_3$, t, 0.98 ppm; C(9)—H, t, 3.83 ppm; C(6)—N(CH$_3$)$_2$, s 2.22 ppm; CH$_2$, CH, m, 1.5–3.3 ppm.

EXAMPLE 31

15 g of dimethylamino-3-ethyl-3-azabicyclo[3.3.1]nonane-9-ol isomeric mixture, i.e. a mixture of 6α,9α; 6α,9β and 6β,9α-ols obtained from the mother liquor(s) of the (re)crystallization from diisopropyl ether in Example 30, is dissolved in 100 ml of chloroform. To this solution 9.93 g of benzoyl chloride is added below 15° C. within 10 minutes. The reaction mixture is allowed to stand at ambient temperature over 12 hours and then the solvent is distilled off. The residue is dissolved in 100 ml of water, acidified to pH 3 with concentrated hydrochloric acid and is extracted three times with 50 ml. portions of dichloromethane to remove the non-basic impurities.

The pH of the aqueous layer is adjusted to 8 with potassium carbonate and extracted three times with 50 ml. portions of dichloromethane. The extracts are combined, dried over magnesium sulfate, filtered and the filtrate is evaporated. The residue, a viscous oil contains two ester-isomers. Hydrochloric acid is added to the residue and the precipitate is recrystallized three times from methanol to yield the 6β-dimethylamino-3-ethyl-9α-benzoyloxy-3-azabicyclo[3.3.1]nonane dihydrochloride. Mp.: 276°–278° C. (decomposition).

EXAMPLE 32

To a mixture of 2.3 g of 6α-dimethylamino-3-ethyl-3-azabicyclo[3.3.1]nonane-9α-ol and 3.3 g of phenylacetic acid ethyl ester of 0.1 g of sodium metal is added in small portions. The reaction mixture is maintained at 90°–100° C. under 1.7 kPa pressure over 4 hours. Then the vacuum is terminated, and 50 ml of 10% aqueous hydrochloric acid is added. The excess of the phenylacetic acid ethyl ester is extracted twice with 50 ml. portions of ether. The aqueous layer is rendered alkaline with potassium carbonate whereupon the ester base separates and is extracted three times with 50 ml. portions of dichloromethane. The extracts are combined, dried over magnesium sulfate, filtered and the filtrate is evaporated. To the residue hydrogen bromide is added to afford 6α-dimethylamino-3-ethyl-9α-phenylacetyloxy-3-azabicyclo[3.3.1]nonane dihydrobromide with a yield of 84.6%. Mp.: 225°–227° C. with decomposition after recrystallization from methanol.

EXAMPLE 33

32 g of an about 80:20 mixture of 6α-dimethylamino-3-butyl-3-azabicyclo[3.3.1]nonan-9-one and 6β-dimethylamino-3-butyl-3-azabicyclo[3.3.1]nonan-9-one prepared according to Example 5, is reduced with 24.8 g of 70% sodium-dihydro-bis(2-methoxyethoxy)aluminate as described in Example 30. The resulting product is purified by vacuum distillation to give 29.5 (92.2%) colorless oil being the mixture of 6α-dimethylamino-3-butyl-3-azabicyclo[3.3.1]nonane-9α-ol, 6α-dimethylamino-3-butyl-3-azabicyclo[3.3.1]nonane-9β-ol and 6β-dimethylamino-3-butyl-3-azabicyclo[3.3.1]nonane-9α-ol. Bp.: 120°–126° C./13 Pa.

EXAMPLE 34

To 18.5 g of the isomeric mixture obtained in Example 33, 100 ml. of chloroform, and under water cooling 10.82 g of benzoyl chloride are added. The reaction mixture is allowed to stand at ambient temperature over 12 hours and is then evaporated in vacuo. The residue is dissolved in water, acidified to pH 3 with concentrated hydrochloric acid and extracted three times with 50 ml. portions of ether to remove the non-basic impurities.

The pH of the aqueous layer is adjusted to 8 with potassium carbonate and is extracted three times with 50 ml. portions of dichloromethane. The combined extract contains the ester components.

With further amount of potassium carbonate the pH of the aqueous layer is adjusted to 10 and is then extracted 3 times with 50 ml. portions of dichloromethane. The combined extract is dried over magnesium sulfate and the solvent is removed in vacuo. The residue is a viscous oil which upon standing crystals to give 6α-dimethylamino-3-butyl-3-azabicyclo[3.3.1]nonane-9α-ol. The product after recrystallization from diisopropyl ether and subsequent vacuum sublimation melts at 72°-73° C.

The structure was confirmed by the aid of $^{13}$C-NMR and $^{1}$H-NMR spectra from which the $^{1}$H-NMR data are as follows:

$^{1}$H-NMR (CDCl$_3$): δ N(3)—(CH$_2$)$_3$—CH$_3$, s, 0.85 ppm; C(6)—N(CH$_3$)$_2$, s, 2.22 ppm; C(9)—$\underline{H}$, t, 3.82 ppm; C$\underline{H}_2$, C$\underline{H}$, m, 1.0–3.3 ppm.

EXAMPLE 35

The combined extract obtained at pH 8 in Example 34, is dried over magnesium sulfate and then the solvent is disstilled off in vacuo to the residue which contains two ester isomers hydrochloric acid is added and the precipitate is recrystallized twice from methanol to yield 6β-dimethylamino-3-butyl-9α-benzoyloxy-3-azabicyclo[3.3.1]nonane dihydrochloride. Mp.: 273°-275° C. (decomposition).

EXAMPLE 36

2.8 g of 6α-dimethylamino-3-butyl-3-azabicyclo[3.3.1]nonane-9α-ol is dissolved in 30 ml of dry pyridine. To this solution 3.22 g of diphenylacetyl chloride is added below 15° C. within 5 minutes. The reaction mixture is allowed to stand at room temperature for 2 hours and is worked up as described in Example 29. The product is isolated as dihydrobromide salt. After recrystallization from ethanol the 6α-dimethylamino-3-butyl-9α-diphenylacetyloxy-3-azabicyclo[3.3.1]nonane dihydrobromide monohydrate sinters at 160° C., melts at 165°-175° C. with effervescence. Yield 86.7%.

EXAMPLE 37

19.8 g of 6α-dimethylamino-3-methyl-3-azabicyclo[3.3.1]nonane-9α-ol is reacted with benzyl chloride as described in Example 10, to give 6α-dimethylamino-3-methyl-9α-benzyloxy-3-azabicyclo[3.3.1]nonane. It is purified by vacuum distillation, bp.: 164°-166° C./20 Pa; n$_D^{25}$=1.5332; yield: 34.5%. Its hygroscopic dihydrobromide salts melts at 155°-161° C. after recrystallization from ethanol.

EXAMPLE 38

To a solution of 5.5 g of 6α-dimethylamino-3-methyl-3-azabicyclo[3.3.1]nonane-9α-ol in 30 ml of ethanol, a solution of 20.8 g (+)-dibenzoyl-D-tartaric acid monohydrate in 30 ml of ethanol is added. The diastereomer salt promply crystals, after standing for 12 hours is filtered, dried and is recrystallized twice from methanol to give (−)-6α-dimethylamino-3-methyl-3-azabicyclo[3.3.1]nonane-9α-ol di-(+)-dibenzoyl-D-tartarate monohydrate with a yield of 56.5%. [α]$_{578}^{25}$= +83° (c=1, methanol); mp.: 147°-150° C.

From the diastereomer salt the respective base is set free with potassium carbonate to give (−)-6α-dimethylamino-3-methyl-3-azabicyclo[3.3.1]nonane-9α-ol which crystals from n-heptane. Mp.: 86°-87° C.; [α]$_{578}^{25}$= −19° (c=2, ethanol).

EXAMPLE 39

5.95 g of (−)-6α-dimethylamino-3-methyl-3-azabicyclo[3.3.1]nonane-9α-ol is dissolved in 50 ml of dry pyridine. To this solution 9.23 g of 3,4,5-trimethoxybenzoyl chloride is added below 15° C. within 10 minutes. The reaction mixture is allowed to stand at room temperature for 1 hour and is worked up as described in Example 29. The resulting (+)-6α-dimethylamino-3-methyl-9α-(3',4',5'-trimethoxybenzoyloxy)-3-azabicyclo[3.3.1]nonane crystals from ethanol, melts at 147°-150° C. [α]$_{578}^{23}$=+23° (c=3, dichloromethane). Yield=65.4%. Its salt with hydrochloric acid crystals as hemihydrate affording the (+)-6α-dimethylamino-3-methyl-9α-(3',4',5'-trimethoxybenzoyloxy)-3-azabicyclo[3.3.1]nonane dihydrochloride. . ½ H$_2$O from a mixture of ethanol and diisopropyl ether and melts at 170°-180° C. with effervescence. [α]$_{578}^{23}$= = +9.0° (c=3, water).

EXAMPLE 40

To 24 g of 6α-dimethylamino-3-methyl-3-azabicyclo[3.3.1]nonane dissolved in 150 ml of ethanol a solution of (−)-dibenzoyl-L-tartaric acid monohydrate in 300 ml of ethanol is added. The diastereomer salt begins to crystal promptly, allowed to stand for 12 hours and then is filtered off and dried. The resulting (+)-6α-dimethylamino-3-methyl-3-azabicyclo[3.3.1]nonane-9α-ol di-(−)-dibenzoyl-L-tartarate monohydrate melts at 147°-149° C. after two recrystallization from methanol. Yield=60.2%. [α]$_{578}^{23}$= −81° (c=1, methanol).

From the diastereomer salt the respective base is set free with potassium carbonate. The resulting (+)-6α-dimethylamino-3-methyl-3-azabicyclo[3.3.1]nonane-9α-ol crystals from n-hexane, melts at 78°-80° C. [α]$_{578}^{23}$=+20° (c=2, dichloromethane).

EXAMPLE 41

To a solution of 4.96 g of (+)-6α-dimethylamino-3-methyl-3-azabicyclo[3.3.1]nonane-9α-ol in 50 ml of dry pyridine, 6.92 g of 3,4,5-trimethoxybenzoyl chloride is added below 15° C., within 10 minutes. The reaction mixture is allowed to stand at room temperature, and is worked up as described in Example 29. The resulting (−)-6α-dimethylamino-3-methyl-9α-(3',4',5'-trimethoxybenzoyloxy)-3-azabicyclo[3.3.1]nonane crystals from ethanol, melts at 146°-147° C. [α]$_{578}^{23}$= = −22° (c=3, dichloromethane). Yield=68.8%. Its salt with hydrochloric acid the (−)-6α-dimethylamino-3-methyl-9α-(3',4',5'-trimethoxybenzoyloxy)-3-azabicyclo-[3.3.1]nonane dihydrochloride hemihydrate (½ H$_2$O) crystals from a mixture of ethanol and diisopropyl ether, and melts at 160°-175° C. with effervescence. [α]$_{578}^{23}$= −8.7 (c=3, water).

What we claim is:

1. An azabicyclo(3.3.1)nonane derivative of the formula (I)

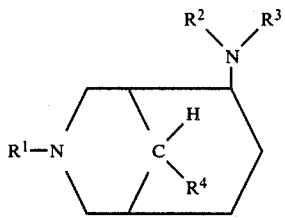

wherein
- $R^1$, $R^2$ and $R^3$ are $C_{1-4}$ alkyl groups which are the same or different, or one of them is a benzyl group and the others are $C_{1-4}$ alkyl groups, and
- $R^4$ is a hydroxy group, or an etherified hydroxy group of the formula $-OR^5$, or an esterified hydroxy group of the formula $-OOCR^6$, in which the etherifying group
- $R^5$ is a phenyl or benzyl group which each can have a trihalomethyl substituent or one more halogen or $C_{1-4}$ alkyl substituents, or is a diphenyl or benzhydryl group, and the esterifying group
- $R^6$ is a $C_{1-8}$ alkyl or a $C_{3-6}$ cycloalkyl group, or a phenyl or benzyl group which each can have a halo-substituent or one or more $C_{1-4}$ alkyl, $C_{1-4}$ alkoxy, nitro or phenyl substituents, or is naphthyl or halogenated or hydrogenated naphthyl group, or a cinnamyl group which can be substituted by a halogen atom or $C_{1-4}$ alkoxy groups, or is a benzhydryl or 1,1-diphenyl-hydroxymethyl group, or is a heterocyclic substituent selected from the group consisting of thenyl, 9-xanthenyl or 3-indolyl-($C_{1-3}$ alkyl) groups, or a stereoisomer and or pharmaceutically acceptable acid addition salt thereof.

2. The compound of the Formula (I) defined in claim 1 which is:
6α-dimethylamino-3-methyl-9α-(3'trifluoromethylphenoxy)-3-azabicyclo[3.3.1]nonane; or
6α-dimethylamino-3-methyl-9α-(3',4',5'-trimethyoxybenzoyloxy)-3-azabicyclo[3.3.1]nonane; or
a pharmaceutically acceptable acid addition salt thereof.

3. The compound of the Formula (I) defined in claim 1 which is 6α-dimethylamino-3-methyl-9α-(3'-trifluoromethylphenoxy)-3-azabicyclo[3.3.1]nonane or the fumarate acid addition salt thereof.

4. The compound of the Formula (I) defined in claim 1 wherein $R^4$ is an etherified hydroxy group of the Formula $-OR^5$, and $R^5$ is a phenyl or benzyl group which each can have a trihalomethyl substituent or one or more halogen or methyl substituents, or is a diphenyl or benzhydryl group, or a stereoisomer or a pharmaceutically acceptable acid addition salt thereof.

5. A compound of the Formula (I)

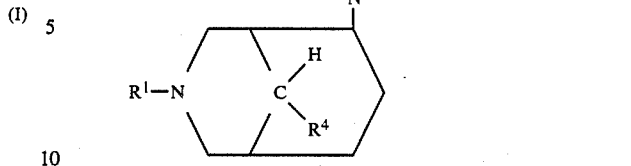

wherein
- $R^1$, $R^2$, and $R^3$ are $C_1$ to $C_4$ alkylgroups which are the same or different, or one of them is a benzyl group and the others are $C_1$ to $C_4$ alkyl groups, and
- $R^4$ is a hydroxy group, or an etherified hydroxy group of the formula $-OR^5$, or an esterified hydroxy group of the formula $-OOCR^6$, in which the etherifying group $R^5$ is a phenyl or benzyl group which each can have a trihalomethyl substituent or one or more halogen substituents, or is a diphenyl or benzhydryl group, and the esterifying group $R^6$ is a $C_1$ to $C_8$ alkyl or a $C_3$ to $C_6$ cycloalkyl group, or a phenyl or benzyl group which each can have a halo substituent or one or more $C_1$ to $C_4$ alkyl, $C_1$ to $C_4$ alkoxy, nitro or phenyl substituents, or is naphthyl or halogenated or hydrogenated naphthyl, or a cinnamyl group which can be substituted by a halogen atom or $C_1$ to $C_4$ alkoxy groups, or is a benzhydryl or 1,1-diphenyl-hydroxymethyl group, or is a heterocyclic substituent selected from the group consisting of thenyl, 9-xanthenyl and 3-indolyl-($C_1$ to $C_3$ alkyl) groups, or a stereoisomer or a pharmaceutically acceptable acid addition salt thereof.

6. An antiarrhythmic pharmaceutical composition containing as active agent a pharmaceutically effective amount of a compound as defined in claim 1, or a stereoisomer of a pharmaceutically acceptable acid addition salt thereof together with a pharmaceutically acceptable inert carrier.

7. An antiarrhythmic method of treatment which comprises the step of administering to a mammal in need of said treatment, a therapeutically effective amount of the compound of the Formula (I) as defined in claim 1 or a stereoisomer or a pharmaceutically acceptable acid addition salt thereof.

8. An antiarrhythmic pharmaceutical composition containing as active agent a pharmaceutically effective amount of a compound of the Formula (I) as defined in claim 5, or a stereoisomer or a pharmaceutically acceptable acid addition salt thereof together with a pharmaceutically acceptable inert carrier.

9. An antiarrhythmic method of treatment which comprises the step of administering to a mammal in need of said treatment, a therapeutically effective amount of the compound of the Formula (I) as defined in claim 5 or a stereoisomer or a pharmaceutically acceptable acid addition salt thereof.

* * * * *